United States Patent [19]

Nakano et al.

[11] Patent Number: 5,668,147
[45] Date of Patent: Sep. 16, 1997

[54] QUINOLINECARBOXYLIC ACID DERIVATIVES AND SALTS THEREOF

[75] Inventors: Jun Nakano; Hideto Fukui; Tetsuo Shibata; Hisato Senda; Tetsuro Maejima; Yayoi Watanuki; Tadashi Arika, all of Kyoto, Japan

[73] Assignee: Kaken Pharmaceutical Co., Ltd., Tokyo, Japan

[21] Appl. No.: 632,474

[22] PCT Filed: Oct. 27, 1994

[86] PCT No.: PCT/JP94/01815

§ 371 Date: Apr. 25, 1996

§ 102(e) Date: Apr. 25, 1996

[87] PCT Pub. No.: WO95/11902

PCT Pub. Date: May 4, 1995

[30] Foreign Application Priority Data

Oct. 28, 1993 [JP] Japan ................ 5-292587
Dec. 28, 1993 [JP] Japan ................ 5-353780

[51] Int. Cl.⁶ .................. C07D 215/233; A61K 31/47
[52] U.S. Cl. ............................ 514/312; 546/156
[58] Field of Search ...................... 546/123, 156; 548/557, 566, 570; 514/312

[56] References Cited

U.S. PATENT DOCUMENTS

| | | | |
|---|---|---|---|
| 4,705,788 | 11/1987 | Schriewer et al. | 514/254 |
| 5,252,734 | 10/1993 | Schriewer et al. | 544/64 |
| 5,290,934 | 3/1994 | Ueda et al. | 546/13 |
| 5,468,861 | 11/1995 | Petersen et al. | 546/156 |
| 5,563,138 | 10/1996 | Ueda et al. | 514/254 |

FOREIGN PATENT DOCUMENTS

| | | |
|---|---|---|
| 0241206 | 10/1987 | European Pat. Off. |
| 0443498 | 8/1991 | European Pat. Off. |
| 62-19583 | 1/1987 | Japan . |
| 63-45261 | 2/1988 | Japan . |
| 63-51370 | 3/1988 | Japan . |
| 63-152318 | 6/1988 | Japan . |
| 3-188074 | 8/1991 | Japan . |
| 4-282384 | 10/1992 | Japan . |
| WOA9510519 | 4/1995 | WIPO . |

OTHER PUBLICATIONS

Cesare et al., Fluoronaphthyridines and quinolones as antibacterial agents. 5. Synthesis and Antimicrobial activity of chiral 1–tert–butyl–6–fluoro–7–substituted naphthyridones, J. Med. Chem., vol. 35, pp. 4205–4213, 1992. 1992.

Remuzon et al., Fluoronaphthyridines and quinolones as antibacterial agents, J. Med. Chem., vol. 34, pp. 29–37, 1991. 1991.

Bouzard et al., Fluoronaphthyridines and quinolones as antibacterial agents, J. Med. Chem., vol. 33, pp. 1344–1352, 1990. 1990.

*Primary Examiner*—Matthew V. Grumbling
*Assistant Examiner*—Deepak R. Rao
*Attorney, Agent, or Firm*—Armstrong, Westerman, Hattori, McLeland & Naughton

[57] ABSTRACT

Quinolinecarboxylic acid derivatives which are represented by the general formula (I)

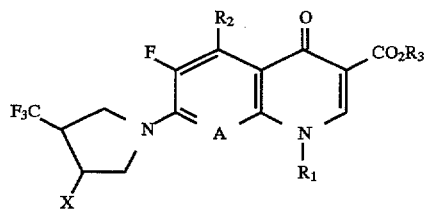

wherein
$R_1$ is a $C_1$ to $C_6$ alkyl group which may be substituted, a $C_2$ to $C_6$ alkenyl group which may be substituted, a $C_3$ to $C_7$ cycloalkyl group which my be substituted or an aryl group which may be substituted, $R_2$ is hydrogen atom; a halogen atom; hydroxyl group which may be protected, amino group or a $C_1$ to $C_6$ alkylamino group each of which may be protected; a $C_1$ to $C_6$ dialkylamino group or a $C_1$ to $C_6$ alkyl group, $R_3$ is hydrogen atom or a $C_1$ to $C_6$ alkyl group, A is nitrogen atom or

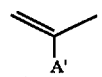

wherein A' is hydrogen atom, a halogen atom, a $C_1$ to $C_6$ alkyl group, a $C_1$ to $C_6$ alkoxyl group which may be substituted, cyano group, or nitro group, and A' may form a ring with $R_1$; the ring may include oxygen atom, nitrogen atom, or sulfur atom as a constituent atom; the ring may be substituted with a $C_1$ to $C_6$ alkyl group, X is hydroxymethyl group; aminomethyl group or amino group each of which may be protected, and salts thereof, and antibacterial agents which comprise the quinolinecarboxylic acid derivatives and salts thereof as active ingredients, and therapeutical methods thereby.

9 Claims, No Drawings

QUINOLINECARBOXYLIC ACID DERIVATIVES AND SALTS THEREOF

This is a national phase application filed under 35 U.S.C 371 of PCT/JP94/01815 filed Oct. 27, 1994.

1. Technical Field

The present invention relates to new quinolinecarboxylic acid derivatives and salts thereof having antibacterial activities, which are useful as a medicine, a veterinary drug, a fishery drug, an agricultural chemical, a preservative, an industrial sterilizer, and the like, and new pyrrolidine derivatives and salts thereof which are intermediates for synthesizing the quinolinecarboxylic acid derivatives.

2. Background Art

Quinolone antibacterial agents developed in recent years, for example, Norfloxacin, Ofloxacin, Ciprofloxacin and Tosufloxacin, which have broad antibacterial spectra and excellent antibacterial activities against gram-positive bacteria and gram-negative bacteria, are now frequently used for treatments of various bacterial infectious diseases. Recently, however, since the third generation cephem drugs, which have a little weak antibacterial activity against gram-positive bacteria, have been generally used, infectious diseases with gram-positive bacteria centering around staphylococcus are increasing; further, appearance of resistant strains such as MRSA (methicillin-resistant staphylococcus) has become a large problem in the field of clinical medicine.

Commercially available quinolone antibacterial agents have a defect of lacking a strong antibacterial activity against gram-positive bacteria such as streptococcus and enterococcus. Additionally, their antibacterial activity against resistant strains such as MRSA are still insufficient. Therefore, a newly developed drug has been desired.

Under these circumstances, the present inventors earnestly made a study for proving an excellent synthetic antibacterial agent in which the above requirements are improved and consequently found that the quinolinecarboxylic acid derivatives and salts thereof shown below have broad antibacterial activity and especially strong antibacterial activity against gram-positive bacteria and resistant strains thereof, particularly MRSA, to complete the present invention.

DISCLOSURE OF THE INVENTION

The present invention provides quinolinecarboxylic acid derivatives which are represented by the general formula (I)

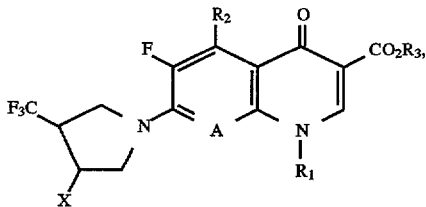

wherein $R_1$ is a $C_1$ to $C_6$ alkyl group which may be substituted, a $C_2$ to $C_6$ alkenyl group which may be substituted, a $C_3$ to $C_7$ cycloalkyl group which may be substituted or an aryl group which may be substituted, $R_2$ is hydrogen atom; a halogen atom; hydroxyl group which may be protected, amino group or a $C_1$ to $C_6$ alkylamino group each of which may be protected; a $C_1$ to $C_6$ dialkylamino group or a $C_1$ to $C_6$ alkyl group, $R_3$ is hydrogen atom or a $C_1$ to $C_6$ alkyl group, A is nitrogen atom or

wherein A' is hydrogen atom, a halogen atom, a $C_1$ to $C_6$ alkyl group, a $C_1$ to $C_6$ alkoxyl group which may be substituted, cyano group, or nitro group, and A' may form a ring with $R_1$; the ring may include oxygen atom, nitrogen atom, or sulfur atom as a constituent atom; the ring may be substituted with a $C_1$ to $C_6$ alkyl group, X is hydroxymethyl group; aminomethyl group or amino group each of which may be protected, and salts thereof, and pyrrolidine derivatives, synthesizing intermediates thereof, which are represented by the general formula (II)

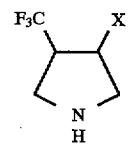

wherein X is hydroxymethyl group, aminomethyl group or amino group each of which may be protected, and salts thereof.

Further, the present invention provides antibacterial agents which comprise the compounds represented by the above general formula (I) or salts thereof as active ingredients and, additionally, methods of treating a bacterial infectious diseases wherein the compounds represented by the above general formula (I) are used.

The feature of the compounds of the present invention is that when a pyrrolidine residue with trifluoromethyl group combines to quinolinecarboxylic acid, the resulting compound has a broad antibacterial spectra and a strong antibacterial activity, especially, against gram-positive bacteria including MRSA.

BEST MODE FOR CARRYING OUT THE INVENTION

Examples of the $C_1$ to $C_6$ alkyl group which may be substituted, represented by $R_1$, in the general formula (I) are, for instance, methyl group, ethyl group, isopropyl group, tert-butyl group, and the like; examples of the substituent are a halogen atom such as fluorine atom, chlorine atom or bromine atom, hydroxyl group, a lower alkoxyl group, and the like. Examples of the $C_1$ to $C_6$ alkyl group which my be substituted are, for instance, difluoromethyl group, 2-fluoroethyl group, 2-hydroxyethyl group, 2-methoxyethyl group, and the like. Examples of the $C_2$ to $C_6$ alkenyl group which my be substituted are, for instance, isopropenyl group, 2-fluoroisopropenyl group, and the like. Examples of the $C_3$ to $C_7$ cycloalkyl group which may be substituted are, for instance, cyclopropyl group, cyclobutyl group, 2-fluorocyclopropyl group, and the like. Example of the aryl group which may be substituted is, for instance, phenyl group which may be substituted with from one to three substituents selected from the group consisting of a halogen atom such as fluorine atom, chlorine atom or bromine atom, a lower alkoxyl group, hydroxyl group, amino group, a lower alkyl group, and nitro group; the concrete examples are phenyl group, 2-fluorophenyl group, 4-fluorophenyl group, 2,4-difluorophenyl group, 2-hydroxyphenyl group, 4-methoxyphenyl group, 4-methylphenyl group, 4-nitrophenyl group, 2,4-dinitrophenyl group, and the like.

Examples of the halogen atom represented by $R_2$ are, for instance, fluorine atom, chlorine atom and the like. Examples of the protective group of hydroxyl group which may be protected are, for instance, acetyl group, tetrahydropyranyl group, and the like. Examples of the protective group of the amino group and the $C_1$ to $C_6$ alkylamino group both of which may be protected are, for instance, acetyl group, tert-butoxycarbonyl group, and the like. Examples of the $C_1$ to $C_6$ alkylamino group and the $C_1$ to $C_6$ dialkylamino group both of which may be protected are, for instance, methylamino group, ethylamino group, dimethylamino group, and the like. Examples of the $C_1$ to $C_6$ alkyl group are, for instance, methyl group, ethyl group, isopropyl group, tert-butyl group, and the like.

Examples of the $C_1$ to $C_6$ alkyl group represented by $R_3$ are, for instance, methyl group, ethyl group, isopropyl group, and the like.

Examples of the halogen atom represented by A' are, for instance, fluorine atom, chlorine atom, bromine atom, and the like. Examples of the $C_1$ to $C_6$ alkyl group are, for instance, methyl group, ethyl group, and the like. Examples of the $C_1$ to $C_6$ alkoxyl group which may be substituted are, for instance, methoxy group, fluoromethoxy group, difluoromethoxy group, ethoxy group, 1-fluoroethoxy group, 2-fluoroethoxy group, and the like. Example structures of the tricyclic quinoline including the ring which can be made by A' and $R_1$ are, for instance, 2,3-dihydro-7-oxy-7H-pyrido[1,2,3-de][1,4]benzoxazines, 2,3-dihydro-7-oxo-7H-pyrido[1,2,3-de][1,4]benzothiazines, and the like.

Examples of the protective group of the aminomethyl group or amino group each of which may be protected represented by X are, for instance, acetyl group, tert-butoxycarbonyl group, and the like.

The quinolinecarboxylic acid derivatives (I) of the present invention can form acid addition salts or base addition salts. Examples of the acid addition salts are, for instance, salts with an inorganic acid such as hydrochloric acid or sulfuric acid, and salts with an organic acid such as acetic acid, trifluoroacetic acid, p-toluenesulfonic acid or methanesulfonic acid. Examples of the base addition salts are, for instance, salts with an alkaline metal such as sodium or potassium, salts with an alkaline earth metal such as magnesium or calcium, ammonium salts, and salts with an organic base containing nitrogen such as trimethylamine, pyridine, N-methylpiperidine, N-methylmorpholine, diethylamine, benzylamine or N,N-dimethylethanolamine.

The quinolinecarboxylic acid derivatives (I) of the present invention have optical isomers because of the asymmetric carbon atoms at the 3-position and 4-position of pyrrolidine ring; concerning the configuration of the 3-position and 4-position of pyrrolidine ring, either cis or trans is useful; the compounds of the present invention include every optical isomer and mixture thereof. A separation of the mixture can be performed using a known procedure.

A process for preparing the quinolinecarboxylic acid derivative represented by the general formula (I) of the present invention is explained below. The process for preparing the compound of the present invention should be appropriately chosen depending on the kind of employed substituent, and the like. Preferable processes are shown below as examples.

[Process 1]

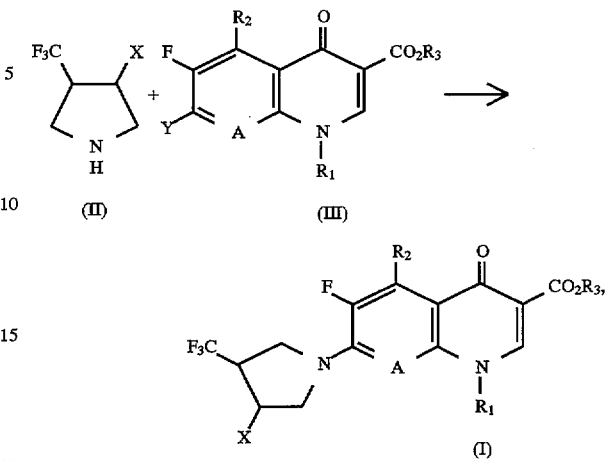

wherein $R_1$, $R_2$, $R_3$, $R_4$, A and X are the same as the above; Y is a halogen atom or a sulfonic acid residue.

The compound of the general formula (I) is prepared by condensation of a quinoline derivative (III) and the pyrrolidine derivative (II). Examples of the halogen atom represented by Y in the formula are fluorine atom, chlorine atom, and the like. Examples of the sulfonic acid residue are methanesulfonic acid residue, p-toluenesulfonic acid residue, 2,4,6-triisopropylbenzenesulfonic acid residue, and the like.

The condensation is performed in an aromatic hydrocarbon such as benzene, toluene or xylene, a lower alcohol such as methanol, ethanol or isopropanol, an ether such as tetrahydrofuran, dioxane or monoglyme, or an aprotic polar solvent such as acetonitril, dimethylformamide, dimethylsulfoxide or sulforane. The reaction temperature is usually from 0° to 200° C., and the reaction time is usually from 10 minutes to 24 hours.

The condensation is performed usually by using from one to 5 equivalents of the pyrrolidine derivative (II) for one equivalent of the quinoline derivative (III) under the presence of a deoxidizer. Examples of the deoxidizer are an alkaline metal hydroxide such as sodium hydroxide or potassium hydroxide, an alkaline earth metal hydroxide such as magnesium hydroxide or calcium hydroxide, an alkaline metal carbonate such as sodium carbonate, sodium bicarbonate, potassium carbonate or potassium bicarbonate, and an organic base such as triethylamine, pyridine, N-methylmorpholine or 1,8-diazabicyclo[5,4,0]undeca-7-ene (DBU). Used mount of the deoxidizer varies depending on the amount of the pyrrolidine derivative (II) and usually is from one to 7 equivalents for one equivalent of the quinoline derivative (III).

[Process 2]

Process for Preparing Compound of General Formula (I) in case $R_3$ is Hydrogen Atom

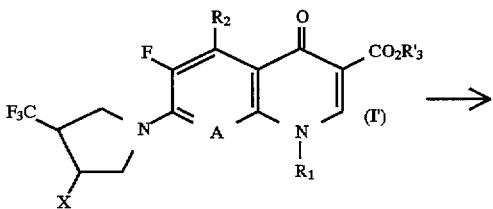

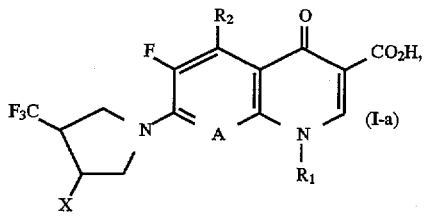

wherein $R_1$, $R_2$, A and X are the same as the above; $R_3'$ is a $C_1$ to $C_6$ alkyl group.

A compound of the general formula (I-a) can be prepared by hydrolyzing a compound of the general formula (I') in which $R_3'$ is a $C_1$ to $C_6$ alkyl group; this hydrolysis can be performed under either acidic or alkaline conditions.

In case the hydrolysis is performed under alkaline conditions, sodium hydroxide, potassium hydroxide, magnesium hydroxide, barium hydroxide, aqueous ammonia, or the like is used as a basic reaction agent, and methanol, ethanol, water, or the like is used as a solvent. The reaction temperature is usually from 0° to 100° C., and the reaction time is usually from 10 minutes to 5 hours.

In case the hydrolysis is performed under acidic conditions, hydrochloric acid, sulfuric acid, formic acid, acetic acid, trifluoroacetic acid, or the like, or a mixture thereof is used as an acidic reaction agent, and a lower alcohol such as methanol, ethanol or isopropanol, or water, or the like is used as a solvent. The reaction temperature is usually from 0° to 130° C., and the reaction time is usually from 10 minutes to 10 hours.

In case the hydrolysis is performed under acidic conditions, an acid addition salt of the compound of the general formula (I-a) wherein X is unprotected aminomethyl group or unprotected amino group could be directly obtained.

[Process 3]

Process for Preparing Compound of General Formula (I) in case $R_3$ is Hydrogen Atom

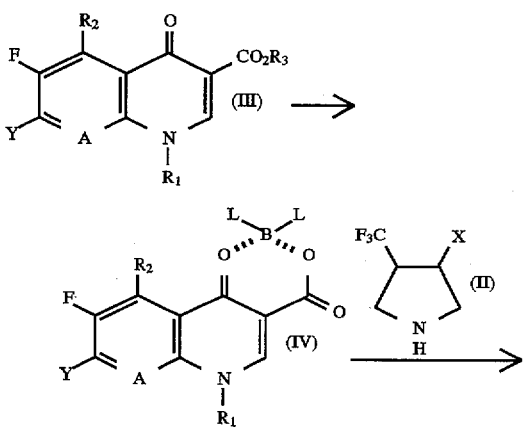

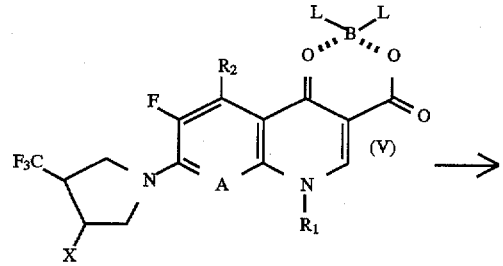

wherein $R_1$, $R_2$, $R_3$, A, X and Y are the same as the above; L is fluorine atom or acetoxyl group.

The compound of the general formula (I-a) can be prepared as follows: the quinoline derivative (III) is converted to a boron chelate compound (IV) by adding a boron reagent thereto, and then the resulting boron chelate compound (IV) is condensed with the pyrrolidine derivative (II) to give its boron chelate (V) followed by treating with a base.

Examples of the boron reagent are boron hydrofluoric acid, boron trifluoride diethyl ether complex, a mixture of boric acid and acetic anhydride, and the like. The used of amount the boron reagent is from 1.2 equivalents to large excess comparing to that of the quinoline derivative (III). The addition is performed in water or an ether solvent such as diethyl ether, tetrahydrofuran or dioxane at from 20° to 100° C., under heating up to 100° C. depending on the necessity. The reaction time is usually from 30 minutes to 24 hours.

The condensation of the boron chelate compound (IV) and the pyrrolidine derivative (II) is performed in a lower alcohol such as methanol, ethanol or isopropanol, an ether such as tetrahydrofuran or monoglyme, an aprotic polar solvent such as acetonitrile, dimethylformamide, dimethylsulfoxide or sulfolane. Usually, from one to 5 equivalents of the pyrrolidine derivative (II) is usually used for one equivalent of the boron chelate compound (IV) under the presence of a deoxidizer. Examples of the deoxidizer are an alkaline metal hydroxide such as sodium hydroxide or potassium hydroxide, an alkaline earth metal hydroxide such as magnesium hydroxide or calcium hydroxide, an alkaline metal carbonate such as sodium carbonate, sodium bicarbonate, potassium carbonate or potassium bicarbonate, and an organic base such as triethylamine, pyridine, N-methylmorpholine or 1,8-diazabicyclo[5,4,0]undeca-7-ene (DBU). Used amount of the deoxidizer is usually from one to 7 equivalents for one equivalent of the boron chelate compound (IV).

Examples of the base which can be used for removing the boron reagent from the boron chelate (V) are an alkaline metal hydroxide such as sodium hydroxide or potassium hydroxide, an alkaline earth metal hydroxide such as magnesium hydroxide or calcium hydroxide, an alkaline metal carbonate such as sodium carbonate or potassium carbonate, and a tertiary amine such as triethylamine, trimethylamine or N-methylmorpholine. Used amount of the base is from 2 equivalents to large excess comparing to one equivalent of the boron chelate (V). This reaction is performed usually using a hydrous lower alcohol as the solvent usually at from 20° to 100° C. The reaction time is from 30 minutes to 12 hours.

[Process 4]

Process for Preparing Compound of General Formula (I) in case X is Aminomethyl Group or Amino Group

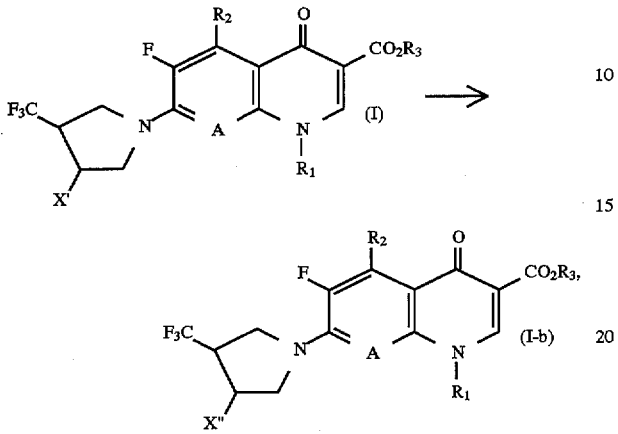

wherein $R_1$, $R_2$, $R_3$ and A are the same as the above; X' is a protected aminomethyl group or a protected amino group, and X" is aminomethyl group or amino group.

A compound (I-b) can be prepared by removing the protecting group from the compound (I) obtained by the process 1, 2 or 3 wherein X is a protected aminomethyl group or a protected amino group.

The removing method of the protecting group can be performed by employing a conventional method according to the used protecting residue. For example, in case the protecting residue is tert-butoxycarbonyl group, treating with an acid such as hydrochloric acid or trifluoroacetic acid is employed, and in case the protecting residue is benzyloxycarbonyl group, a hydrogenation is employed under the presence of a catalyzer such as palladium carbon.

On the other hand, the pyrrolidine derivatives represented by the general formula (II)

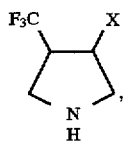

wherein X is the same as the above, which is an intermediate for preparing the compound (I) of the present invention, are novel compounds. They can form acid addition salts. Examples of the salts are, for instance, salts with an inorganic acid such as hydrochloric acid or sulfuric acid, and salts with an organic acid such as acetic acid, trifluoroacetic acid, p-toluenesulfonic acid or methanesulfonic acid.

The pyrrolidine derivatives (II) of the present invention have optical isomers because of the asymmetric carbon atom at the 3-position and 4-position of pyrrolidine ring; concerning the configuration of the 3-position and 4-position of pyrrolidine ring, either cis or trans is useful; the compounds of the present invention include every optical isomer and mixture thereof. A separation of the mixture can be performed using a known procedure.

A process for preparing the pyrrolidine derivative represented by the general formula (II) of the present invention is explained below.

[Process 5]

Process for Preparing Compound of General Formula (II) in case X is Hydroxymethyl Group

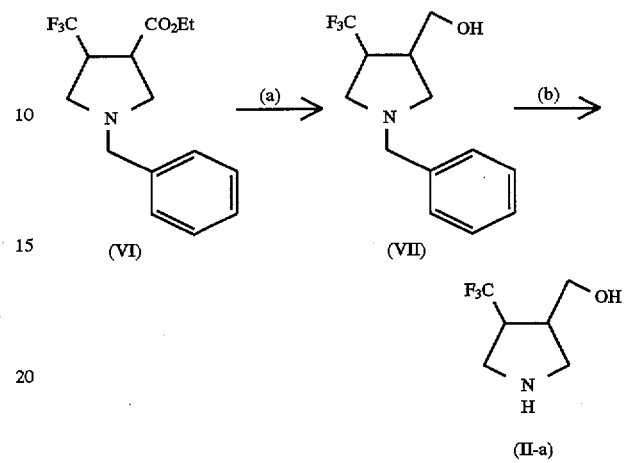

A reducing agent such as lithium aluminium hydride is acted on a compound (VI) to give a compound (VII), and then a hydrogenation is performed to the compound (VII) under the presence of a catalyzer such as palladium carbon to give a compound (II-a). The compound (VI) can be prepared by a known process, for example, Tetrahedron Letters 34 3279–3282 (1993).

[Process 6]

Process for Preparing Compound of General Formula (II) in case X is Protected Aminomethyl Group

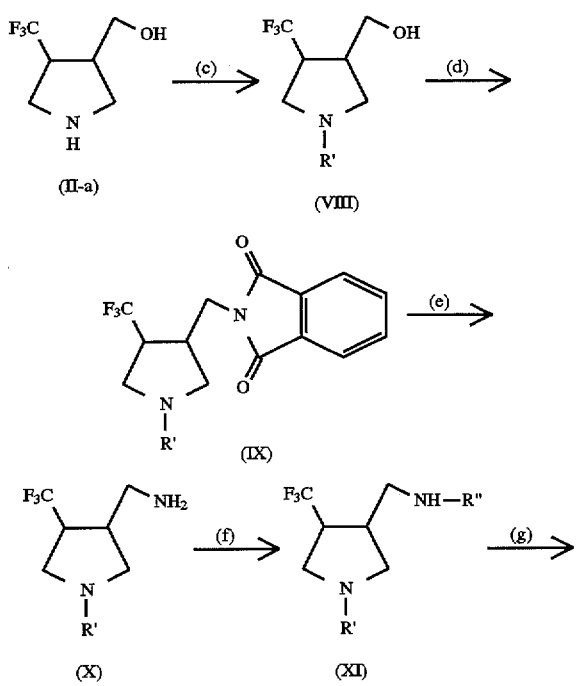

-continued

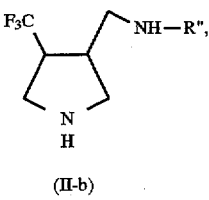

(II-b)

wherein R' and R" are amino-protecting groups; those are either the same or different from each other.

Examples of R' and R" as amino-protecting groups are, for instance, acetyl group, tert-butoxycarbonyl group, benzyloxycarbonyl group, and the like. An amino-protecting group R' is introduced into the compound (II-a) obtained by the Process 5 by a conventional process to give a compound (VIII). The compound (VIII) is reacted with phthalimide to give a compound (IX). Hydrazine is then acted on the compound (IX) to give a compound (X), and then a proper amino-protecting group R" is introduced into the compound (X) by a conventional process to give a compound (XI). The amino-protecting group R' is removed by a conventional process. Then, a compound (II-b) can be obtained.

[Process 7]
Process for Preparing Compound of General Formula (II) in case X is Protected Amino Group

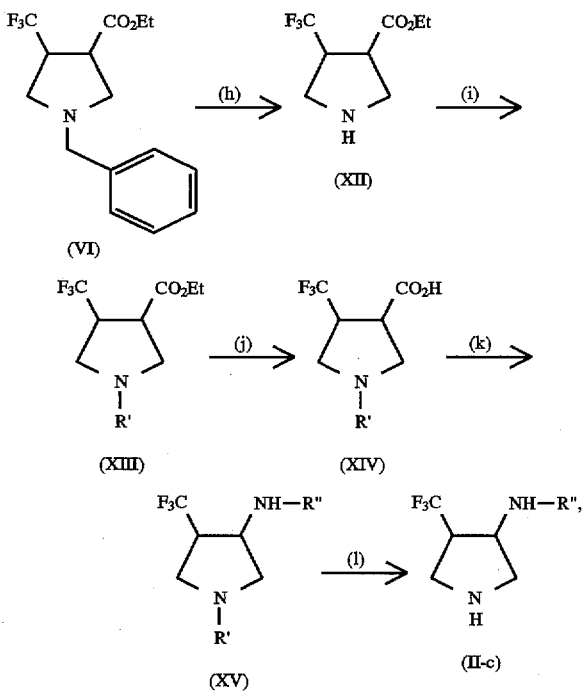

wherein R' and R" are the same as the above.

A hydrogenation is performed to the compound (VI) under the presence of a catalyzer such as palladium carbon to give a compound (XII). An amino-protecting group R' is introduced by a conventional process to give a compound (XIII), and then a hydrolysis of the compound (XIII) is performed to give a compound (XIV). The carboxyl group of the compound (XIV) is converted to acyl azide using a reagent for azidation and then is transformed accompanying denitrification upon heating. The resulting isocyanate is reacted with a proper alcohol to give a compound (XV) wherein R" has a carbonyl group. The amino-protecting group R' is removed from the compound (XV). Then, a compound (II-c) can be prepared.

[Process 8]
Process for Preparing Compound of General Formula (II) in case X is Aminomethyl Group or Amino Group The compound represented by the general formula (II) wherein X is aminomethyl group or amino group can be prepared by removing the amino-protecting group(s) R' and/or R" from either the compound (X), (XI), (II-b), (XV) or (II-c) which is prepared by the Process 6 or 7.

Since the quinolinecarboxylic acid derivatives (I) of the present invention have a strong antibacterial activity, they can be used as a medicine, an antibacterial agent for animals or fish, a preservative for foods, or an agricultural chemical.

When the compound of the present invention is used as a medicine, its dose, which varies depending on ways of administration and pharmaceutical forms, is usually from 10 mg to 1 g per day for an adult. This dose per day is administered once a day or divided into several portions to administer several times a day. If necessary, the dose per day may exceed the above amount. When the compound is used as a veterinary drug, its dose, which varies depending on the species and size of the animal, the kind of the causative bacteria of the infection, or the like, is usually from 1 mg to 200 mg per kg per day.

With respect to antibacterial agents comprising the compounds of the present invention, proper pharmaceutical forms can be chosen according to the way of administration, and their various pharmaceutical forms can be prepared by processes which are usually used for preparing the pharmaceutical forms. The antibacterial agents can be in a form for injection, a solid form, a form for external administration, a form for applying in eyes, a form for applying in nose as well as a form for oral administration such as a tablet, a powder, a granulated powder, a capsule, a liquid or syrup.

Examples of formulae for pharmaceutical forms are shown below.

| [Formulation Example 1] | |
|---|---|
| Compound of Example 12a | 100 g |
| Corn starch | 40 g |
| Abicell | 30 g |
| Magnesium stearate | 3 g |

The compound of Example 12a, corn starch, abicell and magnesium stearate are mixed, and tablets are made from the mixture to give tablets containing 100 mg of the compound of Example 12a per tablet.

| [Formulation Example 2] | |
|---|---|
| Compound of Example 12a | 200 mg |
| Glucose | 250 mg |
| Distilled water for injection | proper amount |

The compound of Example 12a and glucose were dissolved in the distilled water for injection, and then the solution was injected into ampules. After the air was replaced with nitrogen, the ampules were heated for sterilization at 121° C. for 15 minutes to give injections of which constitution is described above.

EXAMPLES

The present invention is specifically explained using Examples and Reference Examples below. Hereinafter, $^1$H-NMR spectra were measured using $d_6$-dimethylsulfoxide (DMSO-$d_6$) or heavy chloroform (CDCl$_3$) solution and tetramethylsilane (TMS) as the internal standard by means of JNM-EX270 type spectrometer (270 MHz, made by JEOL LTD.). The δ value was shown as ppm. Mass spectra were measured by QP1000EX type spectrometer (made by SHIMAZU CORPORATION). Melting points were measured without correction by a micro-melting point meter (made by Yanagimoto Seisakusho).

An Example in which the configuration of the pyrrolidine ring of the product is trans has a number with "a", and an Example in which the configuration of the pyrrolidine ring of the product is cis has a number with "b", hereinafter the same.

Reference Example 1

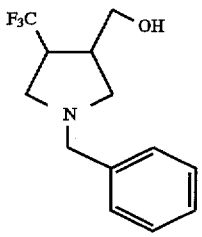

a) Trans-1-benzyl-3-hydroxymethyl-4-trifluoromethylpyrrolidine

In 30 ml of absolute tetrahydrofuran, is suspended 0.36 g (9.50 mmol) of lithium aluminum hydride.

A mixed solution of 2.86 g ( 9.50 mmol) of trans-1-benzyl-4-trifluoromethylpyrrolidine-3-carboxylic acid ethyl ester and 15 ml of absolute tetrahydrofuran is added dropwise to the above suspension over 40 minutes on cooling with ice. After stirring at 0° C. for 1.5 hours, the excess reagent is decomposed by adding several drops of sodium sulfate (decahydrate) and 2N sodium hydroxide. Insoluble matter is removed by filtration under reduced pressure. The filtrate is concentrated under reduced pressure. The resulting residue was purified with silica gel column chromatography (elusion solvent; n-hexane/ethyl acetate (5/1→5/2 (by volume, hereinafter the same))) to give 2.25 g of the objective substance as a colorless powder (yield 91.4%).

Melting point; 52°–54° C.
MS(M/Z); 259(M⁺), 177, 168, 91
¹H-NMR δ(CDCl₃); 2.35–2.60(3H,m), 2.76–2.95(2H,m), 3.07–3.14(2H,m), 3.57–3.63(1H,m), 3.61(2H,s), 3.75(1H, dd, J=3.5, 10.4 Hz), 7.24–7.36(5H,m)

EXAMPLE 1

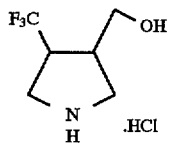

a) Trans-3-hydroxymethyl-4-trifluoromethylpyrrolidine hydrochloride

In 20 ml of ethanol, is dissolved 2.20 g (8.49 mmol) of trans-1-benzyl-3-hydroxymethyl-4-trifluoromethylpyrrolidine, and 1 ml of conc-hydrochloric acid is added to the solution. A hydrogenation is performed by adding 440 mg of 10% palladium carbon to the above solution at 40° C. and 1 atmospheric pressure. Four hours later, the catalyzer was removed by filtration, and the filtrate was concentrated under reduced pressure to give 1.74 g of the objective substance as a colorless powder (yield 99.7%).

Melting point; 87°–90° C.

MS(M/Z); 169(M⁺), 152, 138, 111
¹H-NMR δ(DMSO-d₆); 2.47–2.57(1H,m), 3.12–3.58(7H, m), 5.20(1H,br s), 9.78(2H,br s)

Reference Example 2

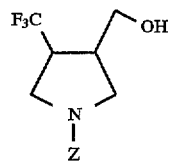

wherein, Z is benzyloxycarbonyl group.

a) Trans-1-benzyloxycarbonyl-3-hydroxymethyl-4-trifluoromethylpyrrolidine

In 40 ml of 2N sodium hydroxide, is dissolved 6.35 g ( 30.9 mmol) of trans-3-hydroxymethyl-4-trifluoromethylpyrrolidine hydrochloride. To the above solution, is added 6.33 g (37.1 mmol) of benzylchloroformate on cooling with ice. The mixture is stirred at room temperature for 15 hours. The reaction mixture is extracted with 100 ml of diethyl ether. The resulting organic phase is washed with saturated aqueous solution of sodium chloride. The washed solution is then dried over anhydrous magnesium sulfate and concentrated under reduced pressure. The residue was purified with silica gel column chromatography (elusion solvent; n-hexane/ethyl acetate (5/3→5/4)) to give 8.04 g of the objective substance as a slightly yellow oily matter (yield 85.9%).

MS(M/Z); 303(M⁺), 258, 212, 91
¹H-NMR δ(CDCl₃); 1.84–1.95(1H,m), 2.63(1H,m), 2.92 (1H,m), 3.40–3.44(1H,m), 3.56–3.73(4H,m), 5.13(2H,s), 7.36(5H,s)

Reference Example 3

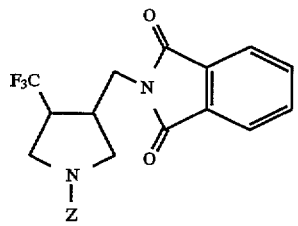

wherein, Z is the same as the above.

a) Trans-1-benzyloxycarbonyl-3-phthalimidomethyl-4-trifluoromethylpyrrolidine

In 250 ml of absolute tetrahydrofuran, is dissolved 8.0 g (26.4 mmol) of trans-1-benzyloxycarbonyl-3-hydroxymethyl-4-trifluoromethylpyrrolidine. To the above solution, are added 4.27 g (29.0 mmol) of phthalimide and 8.30 g (31.7 mmol) of triphenylphosphine. Further, 5.0 ml (31.7 mmol) of azo dicarboxylic acid diethyl ester is added dropwise to the above solution on cooling with ice. After stirring at room temperature for 3 hours, the reaction mixture was concentrated under reduced pressure, and diethyl ether was added to the concentrated mixture to give a precipitate. The resulting precipitate was removed by filtration, and the filtrate was concentrated under reduced pressure. The residue was purified with silica gel column chromatography (elusion solvent; chloroform/n-hexane (4/1→8/1)) to give 9.72 g of the objective substance as a colorless powder (yield 85.2%).

Melting point; 88°–91° C.

MS(M/Z); 432(M⁺), 341, 325, 91

¹H-NMR δ(CDCl₃); 2.72–3.02(2H,m), 3.37(1H, dd, J=5.0, 11.5 Hz), 3.67–3.87(5H,m), 5.13(2H,s), 7.36(5H,s), 7.75–7.90(4H,m)

Reference Example 4

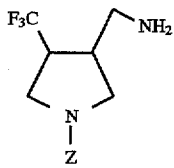

wherein Z is the same as the above.

a) Trans-1-benzyloxycarbonyl-3-aminomethyl-4-trifluoromethylpyrrolidine

In 150 ml of methanol, is dissolved 9.33 g (21.6 mmol) of trans-1-benzyloxycarbonyl-3-phthalimidomethyl-4-trifluoromethylpyrrolidine. To the above solution, is added 2.1 ml (43.2 mmol) of hydrazine monohydrate, and the mixture is stirred at room temperature for 12 hours. The resulting precipitate is removed by filtration, and the filtrate is concentrated under reduced pressure. The residue is dissolved in dichloromethane and washed with water. The washed solution is dried over anhydrous magnesium sulfate and concentrated under reduced pressure. The residue was purified with silica gel column chromatography (elusion solvent; chloroform/methanol (100/2→100/5)) to give 5.89 g of the objective substance as a yellow oily matter (yield 90.3%).

MS(M/Z); 302(M⁺), 285, 211, 91

¹H-NMR δ(CDCl₃); 1.54(2H,br s), 2.45(1H,m), 2.74–2.86(3H,m), 3.34–3.44(1H,m), 3.58–3.71 (3H,m), 5.13(2H,s), 7.36(5H,s)

Reference Example 5

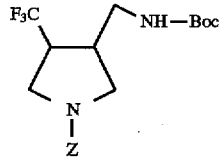

wherein Z is the same as the above; Boc is tert-butoxycarbony group.

a) Trans-1-benzyloxycarbonyl-3-(tert-butoxycarbonylaminomethyl)-4-trifluoromethylpyrrolidine In 60 ml of dichloromethane, is dissolved 5.59 g (19.5 mmol) of trans-1-benzyloxycarbonyl-3-aminomethyl-4-trifluoromethylpyrrolidine. To the above solution, is added 6.38 g (29.3 mmol) of di-tert-butyldicarbonate, and the mixture is stirred at room temperature for 18 hours. The reaction mixture was concentrated under reduced pressure, and the resulting residue was purified with silica gel column chromatography (elusion solvent; chloroform) to give 5.94 g of the objective substance as a slightly yellow oily matter (yield 75.8%).

MS(M/Z); 345(M⁺-tBu), 301, 255, 91

¹H-NMR δ(CDCl₃); 1.44(9H,s), 2.62–2.75(2H,m), 3.10–3.15(1H,m), 3.29(2H,m), 3.64–3.82(3H,m), 4.73(1H, m), 5.13(2H,s), 7.36(5H,s)

EXAMPLE 2

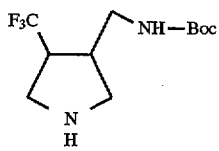

wherein Boc is the same as the above.

a) Trans-3-(tert-butoxycarbonylaminomethyl)-4-trifluoromethylpyrrolidine

In 60 ml of ethanol, is dissolved 5.9 g (14.7 mmol) of trans-1-benzyloxycarbonyl-3-(tert-butoxycarbonylaminomethyl)-4-trifluoromethylpyrrolidine. To the above solution, is added 2.0 g of 10% palladium carbon to perform a hydrogenation at room temperature and 1 atmospheric pressure. Twenty-one hours later, the catalyzer is removed by filtration, and the filtrate is concentrated under reduced pressure. The residue was purified with silica gel column chromatography (elusion solvent; chloroform/methanol (100/1→100/10)) to give 3.04 g of the objective substance as a slightly yellow powder (yield 77.3%).

Melting point; 76°–79° C.

MS(M/Z); 268(M⁺), 211, 138, 57

¹H-NMR δ(CDCl₃); 1.44(9H,s), 2.33–2.57(2H,m), 2.69 (1H,dd,J=6.1, 11.5 Hz), 3.05–3.28(5H,m), 4.82(1H,m)

EXAMPLE 3

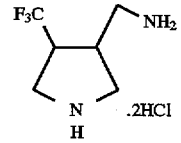

a) Trans-3-aminomethyl-4-trifluoromethylpyrrolidine 2 hydrochloride

In 1 ml of dichloromethane, is dissolved 202 mg (0.754 mmol) of trans-3-(tert-butoxycarbonylaminomethyl)-4-trifluoromethylpyrrolidine. To the above solution, is added 1 ml of trifluoroacetic acid on cooling with ice, and the mixture is stirred at 0° C. for 1 hour. To the reaction mixture, is added 0.19 ml of conc-hydrochloride, and the mixture was concentrated under reduced pressure to give 161 mg of the objective substance as a slightly yellow powder (yield 88.6%).

Melting point; 193°–200° C.

MS(M/Z); 168(M⁺), 151, 138, 82

¹H-NMR δ(DMSO-d₆); 2.76–2.89(1H,m), 3.01–3.15(2H, m), 3.26–3.64(5H,m), 8.45(2H,br s)

Reference Example 6

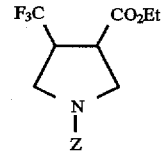

wherein Z is the same as the above.

a) Trans-1-benzyloxycarbonyl-4-trifluoromethylpyrrolidine-3-carboxylic acid ethyl ester In 150 ml of ethanol, is dissolved 15.0 g (49.8 mmol) of trans-1-benzyl-4-trifluoromethylpyrrolidine-3-carboxylic acid ethyl ester. To the above solution, are added 6 ml of conc-hydrochloride and then 3 g of 10% palladium carbon. The mixture is stirred at 40° C. and 1 atmospheric pressure to perform a hydrogenation. Four hours later, the catalyzer is removed by filtration. The filtrate is concentrated under reduced pressure, and the residue was dissolved in 60 ml of water. To the solution, is added 11 g (131 mmol) of sodium bicarbonate. Further, 10.2 g (59.8 mmol) of benzylchloroformate is added to the above solution on cooling with ice. The mixture is stirred at 0° C. for 1 hour and then at room temperature for 11 hours. The reaction mixture is extracted with 150 ml of diethyl ether. The organic phase is washed with saturated aqueous solution of sodium chloride and dried over anhydrous magnesium sulfate. The dried organic phase is concentrated under reduced pressure. The residue was purified with silica gel column chromatography (elusion solvent; n-hexane/ethyl acetate (10/1→5/1)) to give 15.87 g of the objective substance as a colorless oily matter (yield 92.3%).

MS(M/Z); 345(M$^+$), 254, 210, 91

$^1$H-NMR δ(CDCl$_3$); 1.28(3H,t,J=7.1 Hz), 3.22–3.39(2H, m), 3.58–3.92(4H,m), 4.21(2H,q,J=7.1 Hz), 5.14(2H,s), 7.36(5H,s)

Reference Example 7

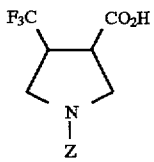

wherein Z is the same as the above.

a) Trans-1-benzyloxycarbonyl-4-trifluoromethylpyrrolidine- 3-carboxylic acid

In 92 ml of ethanol, is dissolved 15.8 g (45.8 mmol) of trans-1-benzyloxycarbonyl-4-trifluoromethylpyrrolidine-3-carboxylic acid ethyl ester. To the above solution, is added 46 ml of 2N sodium hydroxide on cooling with ice. The mixture is stirred at 0° C. for 1 hour and then concentrated under reduced pressure. The residue is dissolved in 100 ml of water. The solution is washed with diethyl ether. The water phase is adjusted to pH 3 with citric acid. The solution is extracted twice with dichloromethane. The organic phases were put together and dried over anhydrous magnesium sulfate. The dried organic phase was concentrated under reduced pressure to give 13.84 g of the objective substance as a colorless powder (yield 95.3%).

Melting point; 118° to 122° C.

MS(M/Z); 317(M$^+$), 210, 91

$^1$H-NMR δ(CDCl$_3$); 3.30–3.39(2H,m), 3.64–3.80(4H,m), 5.14(2H,s), 7.36(5H,s), 7.64(1H,br s)

Reference Example 8

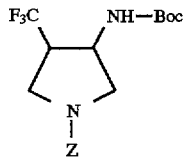

wherein Z and Boc are the same as the above.

a) Trans-1-benzyloxycarbonyl-3-(tert-butoxycarbonylamino)-4-trifluoromethylpyrrolidine In 200 ml of absolute tert-butanol, is dissolved 12.68 g (40 mmol) of trans-1-benzyloxycarbonyl-4-trifluoromethylpyrrolidine-3-carboxylic acid. To the above solution, are added 11.15 g (42 mmol) of diphenylphosphoric acid azide and 6.0 ml (43 mmol) of triethylamine. The mixture is heated under reflux for 19 hours. The reaction mixture is concentrated under reduced pressure. The residue is dissolved in diethyl ether and washed twice with water. The organic phase was dried over anhydrous magnesium sulfate and concentrated under reduced pressure. The residue was purified with silica gel column chromatography (elusion solvent; n-hexane/ethyl acetate (4/1→3/1)) to give 12.15 g of the objective substance as a colorless powder (yield 78.3%).

Melting point; 78°–80° C.

MS(M/Z); 389(M+1), 331, 288, 241

$^1$H-NMR δ(CDCl$_3$); 1.44(9H,s), 2.96(1H,m), 3.35(1H, m), 3.58–3.60(1H,m), 3.75–3.89(2H,m), 4.32–4.39(1H,m), 4.75(1H,br d,J=6.9 Hz), 5.13(2H,s), 7.36(5H,s)

EXAMPLE 4

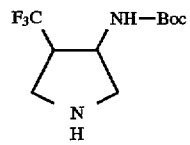

wherein Boc is the same as the above.

a) Trans-3-(tert-butoxycarbonylamino)-4-trifluoromethylpyrrolidine

In 120 ml of ethanol, is dissolved 12.1 g (32.1 mmol) of trans-1-benzyloxycarbonyl-3-(tert-butoxycarbonylamino)-4-trifluoromethylpyrrolidine. To the above solution, is added 1.21 g of 10% palladium carbon to perform a hydrogenation at room temperature and 1 atmospheric pressure. Thirteen hours later, the catalyzer is removed by filtration and the filtrate is concentrated under reduced pressure. To the residue, was added n-hexane. The resulting precipitate was obtained by filtration to give 7.14 g of the objective substance as a colorless powder (yield 90.1%).

Melting point; 95°–97° C.

MS(M/Z); 255(M+1), 197, 181, 137, 57

$^1$H-NMR δ(CDCl$_3$); 1.45(9H,s), 2.69(1H,m), 2.85(1H,br dd,J=4.6, 11.7 Hz), 3.04(1H,dd,J=5.9, 12.2 Hz), 3.19–3.34 (2H,m), 4.08–4.17(1H,m), 4.95(1H,m)

Further, pyrrolidine derivatives were prepared in the same way. The physical properties of the resulting compounds were shown in Table 1.

TABLE 1

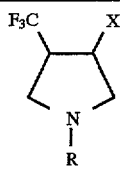

| Example No. | X | R | Addition salt | Yield (%) | m.p. (°C.) | MS(M/Z) | $^1$H-NMR($\delta$) |
|---|---|---|---|---|---|---|---|
| Ref.Ex.1b | CH$_2$OH | CH$_2$Ph | | 90.2 | oily matter | 259(M$^+$), 168, 91, 65 | 2.52–2.64(2H, m), 2.69–2.77(1H, m), 2.85–3.12(4H, m) 3.60–3.73(2H, m), 3.74–3.94(2H, m), 7.22–7.39(5H, m) |
| Ex.1b | CH$_2$OH | H | .HCl | 80.0 | oily matter | 169(M$^+$), 152, 138, 111 | 2.69–2.82(1H, m), 3.17–3.28(1H, m), 3.32–3.51(3H, m), 3.52–3.67(2H, m), 3.68–3.78(1H, m) |
| Ref.Ex.2b | CH$_2$OH | Z | | 73.0 | oily matter | 303(M$^+$), 196, 168, 91 | 1.73–1.98(2H, m), 2.59–2.76(1H, m), 2.88–3.07(1H, m), 3.42–3.57(1H, m), 3.59–3.80(4H, m), 3.83–3.96(1H, m), 5.14(2H, dd, J=12, 19Hz), 7.36(5H,s) |
| Ref.Ex.3b | CH$_2$Pht | Z | | 88.0 | oily matter | 433(M+1), 341, 325, 297, 160, 91 | 2.89–3.14(2H, m), 3.36–3.60(2H, m), 3.64–4.00(4H, m), 5.02–5.21(2H, m), 7.23–7.42(5H, m), 7.68–7.76(2H, m), 7.78–7.90(2H, m) |
| Ref.Ex.4b | CH$_2$NH$_2$ | Z | | 75.0 | oily matter | 303(M+1) 285, 211, 91 | 1.29(2H, br s), 2.42–2.58(1H, m), 2.71–2.85(1H, m), 2.86–3.10(2H, m), 3.29–3.44(1H, m), 3.59–3.84(3H, m), 5.14(2H, dd, J=9, 12Hz), 7.36(5H, s) |
| Ref.Ex.5b | CH$_2$NHBoc | Z | | 74.0 | 107–108 | 403(M+1), 301, 255, 91 57 | 1.43(9H, s), 2.72–3.01(2H, m), 3.18–3.43(3H, m), 3.56–3.88(3H, m), 4.66–4.82(1H, m), 5.13(2H, dd, J=12, 18Hz), 7.38(5H, s) |
| Ex.2b | CH$_2$NHBoc | H | | 85.5 | 80–81 | 268(M$^+$), 211, 195, 138, 82, 57 | 1.44(9H, s), 1.90(1H, br s), 2.39–2.58(1H, m), 2.27–2.92 (2H, m), 3.04–3.40(5H, m), 4.69–4.88(1H, m) |
| Ref.Ex.6b | CO$_2$Et | Z | | 73.0 | oily matter | 345(M$^+$), 254, 210, 91 | 1.26(3H, t, J=7Hz), 3.10–3.33(2H, m), 3.60–3.93(4H, m), 4.19(2H, q, J=7Hz), 5.15(2H, dd, J=12, 18Hz), 7.36(5H, s) |
| Ref.Ex.7b | CO$_2$H | Z | | 89.0 | 121–123 | 317(M$^+$), 272, 226, 210, 182, 138, 91 | 3.24–3.46(2H, m), 3.59–3.72(1H, m), 3.73–3.95(3H, m), 5.14(2H, s), 7.35(5H, s), 8.75(1H, br s) |
| Ref.Ex.8b | NHBoc | Z | | 78.0 | oily matter | 389(M+1), 331, 288, 241, 91 | 1.44(9H, s), 2.86–2.96(1H, m), 3.28–3.44(1H, m), 3.52–3.64(1H, m), 3.72–3.91(2H, m), 4.28–4.40(1H, m), 4.70–4.80(1H, m), 5.13(2H, s), 7.36(5H, s) |
| Ex.4b | NHBoc | H | | 96.0 | 102–103 | 197(M-tBu) 181, 137, 57 | 1.39(9H, s), 2.71–2.81(1H, m), 2.90–3.03(2H, m), 3.10–3.20(1H, m), 3.28–3.41(1H, m), 4.06–4.12(1H, m), 6.24(1H, br s), 7.26(1H, d, J=8Hz) |
| Ex.5a | NH$_2$ | H | .2HCl | 92.1 | 256–260 | 154(M$^+$), 134, 92, 56 | 3.37(1H, dd, J=6.0, 12.2Hz), 3.57(1H, dd, J=5.0, 12.9Hz), 3.62(1H, dd, J=7.3, 12.9Hz), 3.68–3.80(1H, m), 3.87(1H, dd, J=9.2, 12.2Hz), 4.13–4.19(1H, m), 9.43(5H, br s) |

Ph: Phenyl
Z: Benzyloxycarbonyl
Pht: Phthalimido
Boc: tert-Butoxycarbonyl

EXAMPLE 6

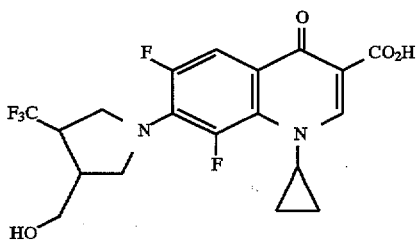

a) 1-Cyclopropyl-6,8-difluoro-1,4-dihydro-7-(trans-3-hydroxymethyl-4-trifluoromethyl-1-pyrrolidinyl)-4-oxoquinoline-3-carboxylic acid In 6 ml of dimethylsulfoxide, is dissolved 283 mg (1 mmol) of 1-cyclopropyl-6,7,8-trifluoro-1,4-dihydro-4-oxoquinoline-3-carboxylic acid. To the above solution, are added 411 mg (2 mmol) of trans-3-hydroxymethyl-4-trifluoromethylpyrrolidine hydrochloride and 0.42 ml (3 mmol) of triethylamine. The mixture is stirred at 50° C. for 18 hours. The reaction mixture was concentrated under reduced pressure. Water was added to the residue. The resulting precipitate was obtained by filtration and washed successively with water, isopropanol and diethyl ether to give 412 mg of the objective substance as a slightly yellow powder (yield 95.4%).

Melting point; 231°–233° C.

MS(M/Z); 432(M$^+$), 388, 319

$^1$H-NMR $\delta$(DMSO-d$_6$); 1.17–1.19(4H,m), 2.50–2.58(1H, m), 3.11–3.14(1H,m), 3.47–3.67(3H,m), 3.84–4.00(3H,m), 4.10–4.12(1H,m), 5.04(1H,t,J=5.3 Hz), 7.77(1H,d,J=13.5 Hz), 8.65(1H,s), 14.86(1H,s)

Further, compounds of Examples 6b–8a were prepared in the same way. The physical properties of the resulting compounds were shown in Table 2.

Reference Example 9

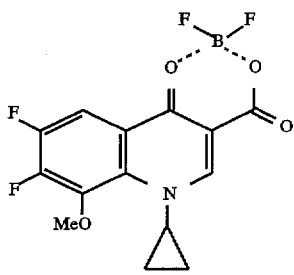

1-Cyclopropyl-6,7-difluoro-1,4-dihydro-8-methoxy-4-oxoquinoline-3-carboxylic acid chelate of boron In 13 ml of 42% boron hydrofluoric acid, was suspended 590 mg (2 mmol) of 1-cyclopropyl-6,7-difluoro-1,4-dihydro-8-methoxy-4-oxoquinoline-3-carboxylic acid. The suspension was stirred at 100° C. for 3 hours, and then, was poured into water to give a precipitate. The resulting precipitate was obtained by filtration. The precipitation was recrystallized from acetone/diethyl ether to give 432 mg of the objective chelate of boron as a colorless powder (yield 63.0%).

Melting point; 220°–225° C.
MS(M/Z); 344(M$^+$), 299, 250
$^1$H-NMR δ(DMSO-d$_6$); 1.28–1.38(4H,m), 4.17(3H,s), 4.49–4.56(1H,m), 8.24–8.31(1H,dd,J=8.25, 9.90 Hz), 9.19 (1H,s)

EXAMPLE 9

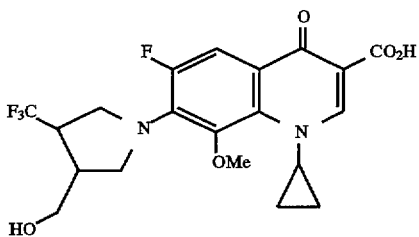

a) 1-Cyclopropyl-6-fluoro-1,4-dihydro-7-(trans-3-hydroxymethyl-4-trifluoromethyl-1-pyrrolidinyl)-8-methoxy- 4-oxoquinoline-3-carboxylic acid In 4 ml of dimethylsulfoxide, is dissolved 344 mg (1 mmol) of the chelate of boron obtained in Reference Example 9. To the solution, are added 411 mg (2 mmol) of trans-3-hydroxymethyl-4-trifluoromethylpyrrolidine hydrochloride and 0.42 ml (3 mmol) of triethylamine. The mixture is stirred at room temperature for 18 hours. The reaction mixture is poured into water to give a precipitate. The resulting yellow precipitate is obtained by filtration. The obtained precipitate is suspended in a mixture of 50 ml of 80% ethanol and 10 ml of triethylamine. The suspension was heated under reflux for 3 hours. The reaction mixture was concentrated under reduced pressure. Isopropanol was added to the residue. The precipitate was obtained by filtration and washed successively with isopropanol and diethyl ether to give 271 mg of the objective substance as a yellow powder (yield 61.0%).

Melting point; 181°–183° C.
MS(M/Z); 444(M$^+$), 400, 355
$^1$H-NMR δ(DMSO-d$_6$); 0.99–1.14(4H,m), 2.49–2.59(1H, m), 3.08–3.19(1H,m), 3.48–3.59(3H,m), 3.61(3H,s), 3.71–3.91(3H,m), 4.12–4.20(1H,m), 5.03(1H,t,J=5.3 Hz), 7.71(1H,d,J=13.3 Hz), 8.69(1H,s), 15.01(1H,s)

Further, compounds of Examples 9b–10b were prepared in the same way. The physical properties of the resulting compounds were shown in Table 2.

EXAMPLE 11

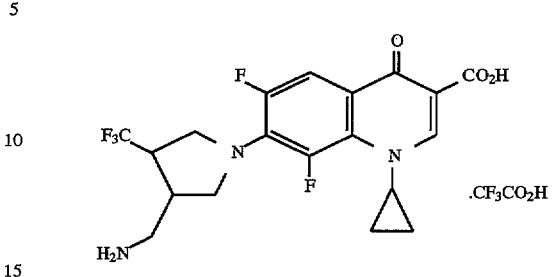

a) 7-(Trans-3-aminomethyl-4-trifluoromethyl-1-pyrrolidinyl)- 1-cyclopropyl-6,8-difluoro-1,4-dihydro-4-oxoquinoline-3-carboxylic acid trifluoroacetate In 2 ml of dichloromethane, is suspended 330 mg (0.606 mmol) of 7-(trans-3-(tertbutoxycarbonylaminomethyl)-4-trifluoromethyl-1-pyrrolidinyl)-1-cyclopropyl-6,8-difluoro-1,4-dihydro-4-oxoquinoline-3-carboxylic acid obtained in Example 10a. To the suspension, is added 2 ml of trifluoroacetic acid on cooling with ice. The mixture is stirred at 0° C. for 1 hour. Diethyl ether was added to the reaction mixture to give a precipitate. The resulting precipitate was obtained by filtration to give 340 mg of the objective substance as a colorless powder (yield 100%).

Melting point; 248°–251° C.
MS(M/Z); 431(M$^+$), 414, 370, 301
$^1$H-NMR δ(DMSO-d$_6$); 1.18–1.20(4H,m), 2.70–2.78(1H, m), 3.01–3.15(2H,m), 3.30(1H,m), 3.66(1H,m), 3.78–3.82 (1H,m), 3.95–4.03(2H,m), 4.09–4.11(1H,m), 7.80(1H,d,J= 13.2 Hz), 8.08(2H,br s), 8.66(1H,s)

EXAMPLE 12

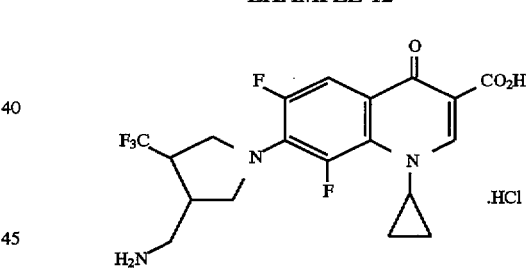

a) 7-(Trans-3-aminomethyl-4-trifluoromethyl-1-pyrrolidinyl)-1-cyclopropyl-6,8-difluoro-1,4-dihydro-4-oxoquinoline-3-carboxylic acid hydrochloride In 4 ml of methanol, is suspended 80 mg (0.147 mmol) of 7-(trans-3-aminomethyl-4-trifluoromethyl-1-pyrrolidinyl)-1-cyclopropyl-6,8-difluoro-1,4-dihydro-4-oxoquinoline-3-carboxylic acid trifluoroacetate obtained in Example 11a. To the suspension, is added 0.02 ml of conc-hydrochloric acid to dissolve the suspension. The reaction liquid is concentrated under reduced pressure. The residue was dissolved in 5 ml of methanol. Diethyl ether was added to the solution to give a precipitate. The resulting precipitate was obtained by filtration to give 65 mg of the objective substance as a slightly yellow powder (yield 94.7%).

Melting point; 241°–245° C.
MS(M/Z); 431(M$^+$), 414, 370, 301
$^1$H-NMR δ(DMSO-d$_6$); 1.18–1.21(4H,m), 2.77–2.82(1H, m), 3.06(2H,m), 3.37–3.42(1H,m), 3.68–3.74(1H,m), 3.81 (1H,m), 3.96–4.04(2H,m), 4.10–4.12(1H,m), 7.81(1H,d,J= 13.3 Hz), 8.22(3H,br s), 8.67(1H,s), 14.79(1H,br s)

Further, compounds of Examples 11b–35a were prepared in the same way. The physical properties of the resulting compounds were shown in Tables 2 and 3.

EXAMPLE 34

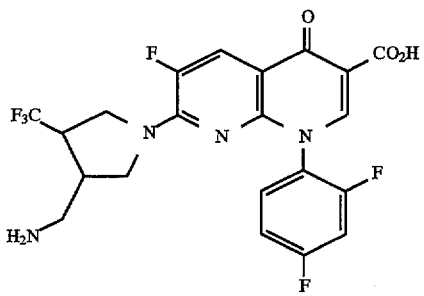

wherein Boc is the same as the above.

a) 7-(Trans-3-(tert-butoxycarbonylamino)-4-trifluoromethyl-1-pyrrolidinyl)-1-(2,4-difluorophenyl)-6-fluoro-1,4-dihydro-4-oxo-1,8-naphthylidine-3-carboxylic acid In 40 ml of ethanol, is dissolved 400 mg (0.676 mmol) of 7-(trans-3-(tert-butoxycarbonylamino)-4-trifluoromethyl-1-pyrrolidinyl)-1-(2,4-difluorophenyl)-6-fluoro-1,4-dihydro-4-oxo-1,8-naphthylidine-3-carboxylic acid methyl ester obtained in Example 33a. To the solution, is added 0.5 ml of 2N sodium hydroxide. The solution is stirred at 40° C. for 1 hour. The reaction liquid is concentrated under reduced pressure. Water is added to the residue. The resulting precipitate is obtained by filtration and washed successively with water and diethyl ether. The resulting colorless precipitate is suspended in water. The suspension is adjusted to pH 4 with acetic acid and extracted with chloroform. The organic phase is dried over anhydrous magnesium sulfate. The dried organic phase is concentrated under reduced pressure. Isopropanol was added to the residue. The resulting precipitate was obtained by filtration to give 189 mg of the objective substance as a colorless powder (yield 48.9%).

Melting point; 221°–222° C.

MS(M/Z); 572($M^+$), 528, 472, 411

$^1$H-NMR δ(DMSO-$d_6$); 1.38(9H,s), 3.15–4.34(6H,m), 7.31–7.41(2H,m), 7.59(1H,m), 7.77–7.85(1H,m), 8.13(1H, d,J=12.2 Hz), 8.85(1H,s), 15.05(1H,s)

TABLE 2

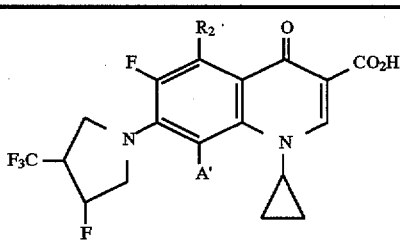

| Ex. No. | X | A' | $R_2$ | Addition salt | Yield (%) | m.p. (°C.) | MS(M/Z) | $^1$H-NMR(δ) |
|---|---|---|---|---|---|---|---|---|
| 6b | $CH_2OH$ | F | H | | 90.6 | 266–267 | 432($M^+$), 388, 319 | 1.08–1.27(4H, m), 2.62–2.78(1H, m), 3.32–3.55(2H, m), 3.62–3.95(4H, m), 3.97–4.16(2H, m), 4.90(1H, t, J=5Hz), 7.75(1H, d, J=13Hz), 8.63(1H, s), 14.89(1H, s) |
| 7a | $CH_2OH$ | Cl | H | | 78.9 | 181–183 | 448($M^+$), 404, 337 | 0.95–1.24(4H, m), 2.50–2.58(1H, m), 3.04–3.15(1H, m), 3.47–3.60(3H, m), 3.67–3.79(2H, m), 3.84–3.92(1H, m), 4.33–4.43(1H, m), 5.02(1H, t, J=5.3Hz), 7.92(1H, d, J=12.9Hz), 8.83(1H, s), 14.60(1H, s) |
| 7b | $CH_2OH$ | Cl | H | | 47.7 | 173–175 | 448($M^+$), 404 | 0.91–1.15(2H, m), 1.22–1.31(2H, m), 2.64–2.81(1H, m), 3.37–3.58(2H, m), 3.63–4.00(5H, m), 4.30–4.45(1H, m), 4.82–4.96(1H, m), 7.90(1H, d, J=13Hz), 8.83(1H, s), 14.66(1H, s) |
| 8a | $CH_2OH$ | F | $NH_2$ | | 70.9 | 239–242 | 447($M^+$), 402, 352 | 1.07–1.11(4H, m), 2.54–2.55(1H, m), 3.07–3.14(1H, m), 3.45–3.63(3H, m), 3.81–4.01(4H, m), 5.02(1H, t, J=5.3Hz), 7.20(2H, br s), 8.48(1H, s), 14.77(1H, s) |
| 9b | $CH_2OH$ | MeO | H | | 75.0 | 205–207 | 444($M^+$), 413, 400, 355 | 0.98–1.17(4H, m), 2.66–2.78(1H, m), 3.30–3.60(2H, m), 3.57(3H, s), 3.65–3.94(5H, m), 4.09–4.20(1H, m), 4.85–4.92(1H, m), 7.70(1H, d, J=13Hz), 8.68(1H, s), 15.08(1H, s) |
| 10a | $CH_2NHBoc$ | F | H | | 71.9 | 193–195 | 531($M^+$), 474, 431, 370 | 1.16–1.19(4H, m), 1.39(9H, s), 2.56–2.63(1H, m), 3.10–3.23(3H, m), 3.56(1H, m), 3.80(2H, m), 3.94–4.02(1H, m), 4.10–4.12(1H, m), 7.17(1H, br t, J=5.9Hz), 7.77(1H, d, J=13.2Hz), 8.65(1H, s), 14.84(1H, s) |
| 10b | $CH_2NHBoc$ | F | H | | 97.9 | 232–234 | 531($M^+$), 474, 431, 370, 57 | 1.10–1.26(4H, m), 1.37(9H, s), 2.62–2.77(1H, m), 2.98–3.13(1H, m), 3.20–3.50(2H, m), 3.64–3.93(3H, m), 3.98–4.16(2H, m), 7.00–7.11(1H, m), 7.75(1H, d, J=13Hz), 8.63(1H, s), 14.89(1H, s) |
| 11b | $CH_2NH_2$ | F | H | .$CF_3COOH$ | 91.7 | 224–225 | 431($M^+$), 414, 370, 301 | 1.11–1.28(4H, m), 2.78–2.95(1H, m), 2.96–3.20(2H, m), 3.45–3.64(1H, m), 3.74–3.95(3H, m), 4.00–4.15(2H, m), 7.79(1H, d, J=14Hz), 8.01(3H, br s), 8.66(1H, s), 14.84(1H, br s) |
| 12b | $CH_2NH_2$ | F | H | .HCl | 96.1 | 180–182 | 431($M^+$), 414, 370, 301 | 1.05–1.30(4H, m), 2.90–3.20(3H, m), 3.48–3.68(1H, m), 3.78–4.20(5H, m), 7.77(1H, d, J=13Hz), 8.33(3H, br s), |

TABLE 2-continued

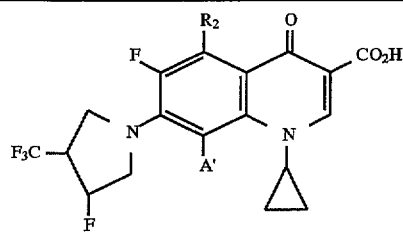

| Ex. No. | X | A' | $R_2$ | Addition salt | Yield (%) | m.p. (°C.) | MS(M/Z) | $^1$H-NMR(δ) |
|---|---|---|---|---|---|---|---|---|
| 13a | $CH_2NHBoc$ | Cl | H | | 83.0 | 208–210 | 547($M^+$), 490, 429, 385 | 8.64(1H, s), 14.85(1H, br s) 0.98–1.21(4H, m), 1.37(9H, s), 2.56–2.63(1H, m), 3.12–3.17(3H, m), 3.39–3.45(1H, m), 3.61–3.76(2H, m), 3.88–3.95(1H, m), 4.36–4.40(1H, m), 7.16(1H, br t, J=5.6Hz), 7.92(1H, d, J=12.5Hz), 8.83(1H, s), 14.56(1H, s) |
| 13b | $CH_2NHBoc$ | Cl | H | | 76.7 | 211–213 | 547($M^+$), 490, 429, 385 57 | 0.89–1.05(2H, m), 1.11–1.26(2H, m), 1.37(9H, s), 2.65–2.80(1H, m), 3.00–3.16(1H, m), 3.20–3.36(1H, m), 3.39–3.53(1H, m), 3.56–3.68(1H, m), 3.69–3.97(3H, m), 4.33–4.42(1H, m), 7.00–7.12(1H, m), 7.90(1H, d, J=13Hz), 8.82(1H, s), 14.65(1H, s) |
| 14a | $CH_2NH_2$ | Cl | H | .$CF_3COOH$ | 97.5 | 230–232 | 447($M^+$), 430, 386, 317 | 0.99–1.22(4H, m), 2.70–2.77(1H, m), 3.02–3.10(2H, m), 3.29–3.40(1H, m), 3.48–3.54(1H, m), 3.66(1H, dd, J=4.6, 10.9Hz), 3.83–3.95(2H, m), 4.39–4.43(1H, m), 7.96(1H, d, J=12.5Hz), 8.85(1H, s) |
| 14b | $CH_2NH_2$ | Cl | H | .$CF_3COOH$ | 91.5 | 209–210 | 447($M^+$), 430, 386, 317 | 0.95–1.06(2H, m), 1.16–1.26(2H, m), 2.85–3.06(2H, m), 3.10–3.21(1H, m), 3.51–3.74(2H, m), 3.76–3.86(2H, m), 3.90–3.99(1H, m), 4.35–4.45(1H, m), 7.94(1H, d, J=13Hz), 8.00(3H, br s), 8.85(1H, s), 14.51(1H, br s) |
| 15a | $CH_2NH_2$ | Cl | H | .HCl | 79.8 | 202–206 | 447($M^+$), 430, 386, 317 | 1.00–1.24(4H, m), 2.76–2.81(1H, m), 3.06(2H, m), 3.35–3.43(1H, m), 3.51–3.57(1H, m), 3.65(1H, dd, J=4.8, 10.8Hz), 3.84–3.96(2H, m), 4.38–4.43(1H, m), 7.96(1H, d, J=12.4Hz), 8.21(3H, br s), 8.86(1H, s), 14.53(1H, br s) |
| 15b | $CH_2NH_2$ | Cl | H | .HCl | 69.7 | 173–176 | 448(M+1), 430, 386, 317 | 0.85–1.01(2H, m), 1.16–1.30(2H, m), 2.89–3.21(3H, m), 3.55–4.00(5H, m), 4.31–4.56(1H, m), 7.92(1H, d, J=13Hz), 8.32(3H, br s), 8.84(1H, s), 14.57(1H, br s) |
| 16a | $CH_2NHBoc$ | F | $NH_2$ | | 96.3 | 182–184 | 546($M^+$), 473, 428, 384 | 1.08–1.15(4H, m), 1.35(9H, s), 2.56–2.58(1H, m), 3.09–3.19(3H, m), 3.51(1H, m), 3.76(2H, m), 3.89–3.90(2H, m), 7.17–7.22(3H, m), 8.48(1H, s), 14.77(1H, s) |
| 17a | $CH_2NH_2$ | F | $NH_2$ | .$CF_3COOH$ | 81.9 | 233–235 | 446($M^+$), 429, 248 | 1.10–1.22(4H, m), 2.70–2.75(1H, m), 3.00–3.05(2H, m), 3.27(1H, m), 3.60(1H, m), 3.73–3.79(1H, m), 3.90–3.97(3H, m), 7.24(2H, br s), 8.03(3H, br s), 8.50(1H, s), 14.72(1H, br s) |
| 18a | $CH_2NH_2$ | F | $NH_2$ | .HCl | 91.9 | 241–244 | 446($M^+$), 429, 248 | 1.03–1.12(4H, m), 2.76–2.81(1H, m), 3.05(2H, m), 3.43–3.46(1H, m), 3.63(1H, m), 3.75(1H, dd, J=4.8, 10.8Hz), 3.91–4.01(3H, m), 7.24(2H, br s), 8.28(3H, br s), 8.49(1H, s), 14.73(1H, br s) |
| 19a | $CH_2NHBoc$ | MeO | H | | 78.6 | 179–181 | 543($M^+$), 486, 443, 425 | 1.01–1.14(4H, m), 1.39(9H, s), 2.60–2.62(1H, m), 3.12–3.21(3H, m), 3.44(1H, m), 3.62(3H, s), 3.66–3.70(1H, m), 3.77–3.83(1H, m), 3.89–3.96(1H, m), 4.16–4.35(1H, m), 7.16(1H, m), 7.72(1H, d, J=13.2Hz), 8.69(1H, s), 15.00(1H, s) |
| 19b | $CH_2NHBoc$ | MeO | H | | 87.7 | 221–222 | 543($M^+$), 486, 443, 425 57 | 0.92–1.15(4H, m), 1.37(9H, s), 2.63–2.78(1H, m), 3.00–3.14(1H, m), 3.19–3.32(1H, m), 3.36–3.50(1H, m), 3.54–3.66(1H, m), 3.58(3H, s), 3.68–3.90(3H, m), 4.06–4.18(1H, m), 7.01–7.09(1H, m), 7.70(1H, d, J=14Hz), 8.67(1H, s), 15.01(1H, s) |
| 20a | $CH_2NH_2$ | MeO | H | .$CF_3COOH$ | 98.3 | 218–220 | 443($M^+$), 426, 399, 382 | 1.00–1.14(4H, m), 2.70–2.78(1H, m), 3.01–3.15(2H, m), 3.30(1H, m), 3.48–3.54(1H, m), 3.63(3H, s), 3.72(1H, dd, J=4.8, 11.1Hz), 3.87–3.94(2H, m), 4.12–4.19(1H, m), 7.57(1H, d, J=13.2Hz), 8.01(2H, br s), 8.71(1H, s) |
| 20b | $CH_2NH_2$ | MeO | H | .$CF_3COOOH$ | 86.8 | 220–224 | 443($M^+$), 426, 399, 382 | 0.98–1.20(4H, m), 2.83–3.06(2H, m), 3.10–3.20(1H, m), 3.52–3.86(4H, m), 3.65(3H, s), 3.89–3.98(1H, m), 4.10–4.20(1H, m), 7.74(1H, d, J=14Hz), 8.00(3H, br s), 8.70(1H, s), 14.85(1H, br s) |
| 21a | $CH_2NH_2$ | MeO | H | .HCl | 88.6 | 218–221 | 443($M^+$), 426, 399, 382 | 1.04–1.15(4H, m), 2.77–2.82(1H, m), 3.06(2H, m), 3.37–3.40(1H, m), 3.50–3.56(1H, m), 3.64(3H, s), 3.71(1H, dd, J=5.1, 11.1Hz), 3.88–3.95(2H, m), 4.16–4.17(1H, m), 7.75(1H, d, J=13.2Hz), 8.18(3H, br s), 8.70(1H, s), 14.95(1H, br s) |
| 21b | $CH_2NH_2$ | MeO | H | .HCl | 81.7 | 188–192 | 443($M^+$), 426, 399, 382 | 0.98–1.20(4H, m), 2.88–3.18(3H, m), 3.33–4.00(5H, m), 3.64(3H, s), 4.11–4.22(1H, m), 7.74(1H, d, J=14Hz), |

TABLE 2-continued

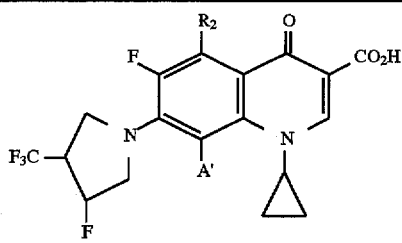

| Ex. No. | X | A' | R₂ | Addition salt | Yield (%) | m.p. (°C.) | MS(M/Z) | ¹H-NMR(δ) |
|---|---|---|---|---|---|---|---|---|
| 22a | NHBoc | F | H | | 99.6 | 210–212 | 517(M⁺), 417, 400, 356 | 8.16(3H, br s), 8.69(1H, s), 14.85(1H, br s) 1.16–1.19(4H, m), 1.41(9H, s), 3.16–3.22(1H, m), 3.63(1H, m), 3.83–4.11(4H, m), 4.33–4.39(1H, m), 7.45(1H, d, J=7.9Hz), 7.77(1H, d, J=13.5Hz), 8.65(1H, s), 14.83(1H, s) |
| 22b | NHBoc | F | H | | 95.0 | 201–203 | 517(M⁺), 460, 444, 416 400, 356, 57 | 1.10–1.29(4H, m), 1.41(9H, s), 3.09–3.28(1H, m), 3.57–3.70(1H, m), 3.81–4.19(4H, m), 4.29–4.46(1H, m), 7.44(1H, d, J=8Hz), 7.78(1H, d, J=14Hz), 8.65(1H,s), 14.83(1H, s) |
| 23a | NH₂ | F | H | .CF₃COOH | 94.1 | 206–208 | 417(M⁺), 373, 234, 192 | 1.17–1.20(4H, m), 3.45–3.50(1H, m), 3.76–3.86(2H, m), 4.06–4.22(4H, m), 7.83(1H, d, J=13.4Hz), 8.68(1H, s) |
| 23b | NH₂ | F | H | .CF₃COOH | 84.4 | 218–220 | 417(M⁺), 373, 234 | 1.11–1.28(4H, m), 3.35–3.57(1H, m), 3.70–3.89(2H, m), 4.00–4.22(4H, m), 7.83(1H, d, J=11.5Hz), 8.50(3H, br s), 8.68(1H, s), 14.72(1H, br s) |
| 24b | NH₂ | F | H | .HCl | 93.5 | 214–216 | 417(M⁺), 373, 234, 192 | 1.11–1.29(4H, m), 3.46–3.66(1H, m), 3.68–4.26(6H, m), 7.83(1H, d, J=13Hz), 8.68(1H, s), 8.78(3H, br s), 14.55(1H, br s) |
| 25a | NHBoc | Cl | H | | 55.5 | 232–234 | 533(M⁺), 460, 416, 372 | 0.98–1.22(4H, m), 1.41(9H, s), 3.18–3.24(1H, m), 3.51–3.57(1H, m), 3.76–3.91(3H, m), 4.32–4.40(2H, m), 7.46(1H, d, J=8.3Hz), 7.92(1H, d, J=12.9Hz), 8.84(1H, s), 14.58(1H, s) |
| 25b | NHBoc | Cl | H | | 60.0 | 230–231 | 533(M⁺), 489, 416, 372 | 0.90–1.08(2H, m), 1.10–1.30(2H, m), 1.41(9H, s), 3.11–3.29(1H, m), 3.47–3.60(1H, m), 3.74–3.94(3H, m), 4.28–4.46(2H, m), 7.43(1H, d, J=9Hz), 7.93(1H, d, J=13Hz), 8.83(1H, s), 14.56(1H, s) |
| 26a | NH₂ | Cl | H | .CF₃COOH | 98.1 | 220–222 | 433(M⁺), 389, 250, 208 | 1.00–1.22(4H, m), 3.40–3.49(1H, m), 3.67(1H, dd, J=5.3, 10.6Hz), 3.79(1H, dd, J=4.0, 10.9Hz), 3.97–4.15(3H, m), 4.39–4.44(1H, m), 7.98(1H, d, J=12.5Hz), 8.86(1H, s) |
| 26b | NH₂ | Cl | H | .CF₃COOH | 98.6 | 207–210 | 433(M⁺), 389, 322, 250 208 | 0.94–1.06(2H, m), 1.13–1.28(2H, m), 3.32–3.54(1H, m), 3.63–3.71(1H, m), 3.72–3.83(1H, m), 3.96–4.05(1H, m), 4.06–4.18(1H, m), 4.34–4.46(1H, m), 7.98(1H, d, J=13Hz), 8.58(3H, br s), 8.86(1H, s), 14.45(1H, br s) |
| 27b | NH₂ | Cl | H | .HCl | 89.9 | 155–158 | 433(M⁺), 389, 291, 250 208 | 0.96–1.08(2H, m), 1.16–1.27(2H, m), 3.32–3.85(3H, m), 3.95–4.19(3H, m), 4.35–4.47(1H, m), 7.98(1H, d, J=12Hz), 8.69(1H, br s), 8.86(1H, s), 14.30(1H, br s) |
| 28a | NHBoc | F | NH₂ | | 91.2 | 198–200 | 532(M⁺), 459, 229 | 1.07–1.17(4H, m), 1.41(9H, s), 3.14–3.20(1H, m), 3.60(1H, m), 3.78–3.98(4H, m), 4.31–4.37(1H, m), 7.21(2H, br s), 7.42(1H, d, J=7.9Hz), 8.48(1H, s), 14.72(1H, br s) |
| 29a | NH₂ | F | NH₂ | .CF₃COOH | 85.7 | 224–225 | 432(M⁺), 387, 229 | 1.04–1.17(4H, m), 3.38–3.48(1H, m), 3.73–3.82(2H, m), 4.00–4.16(4H, m), 7.49(2H, br s), 8.51(1H, s), 8.58(3H, br s), 14.58(1H, br s) |
| 30a | NHBoc | MeO | H | | 88.8 | 225–227 | 529(M⁺), 429, 412, 368 | 0.96–1.18(4H, m), 1.41(9H, s), 3.17–3.23(1H, m), 3.53–3.58(1H, m), 3.62(3H, s), 3.82–3.85(3H, m), 4.15–4.17(1H, m), 4.34–4.40(1H, m), 7.46(1H, d, J=8.3Hz), 7.17(1H, d, J=13.5Hz), 8.69(1H, s), 15.01(1H, s) |
| 30b | NHBoc | MeO | H | | 81.3 | 227–228 | 529(M⁺), 429, 412, 368 57 | 0.90–1.25(4H, m), 1.41(9H, s), 3.11–3.26(1H, m), 3.50–3.68(1H, m), 3.62(3H, s), 3.75–3.91(3H, m), 4.09–4.21(1H, m), 4.29–4.44(1H, m), 7.44(1H, d, J=8Hz), 7.72(1H, d, J=14Hz), 8.68(1H, s), 14.98(1H, s) |
| 31a | NH₂ | MeO | H | .CF₃COOH | 98.3 | 224–226 | 429(M⁺), 385, 337 | 0.99–1.13(4H, m), 3.42–3.68(2H, m), 3.63(3H, s), 3.85(1H, dd, J=4.0, 11.2Hz), 4.00–4.18(4H, m), 7.77(1H, d, J=13.5Hz), 8.54(2H, br s), 8.71(1H, s) |
| 31b | NH₂ | MeO | H | .CF₃COOH | 99.4 | 199–201 | 429(M⁺), 385, 337 | 0.95–1.20(4H, m), 3.40–3.58(1H, m), 3.59–3.71(1H, m), 3.63(3H, s), 3.80–3.92(1H, m), 3.96–4.23(4H, m), 7.75(1H, d, J=14Hz), 8.58(3H, br s), 8.71(1H, s), 14.94(1H, br s) |
| 32b | NH₂ | MeO | H | .HCl | 68.9 | 204–206 | 429(M⁺), 385, 149 | 0.96–1.19(4H, m), 3.34–3.76(2H, m), 3.64(3H, s), 3.80–3.91(1H, m), 3.95–4.21(4H, m), 7.77(1H, d, J=14Hz), 8.71(1H, s), 8.78(3H, br s), 14.94(1H, br s) |

TABLE 3

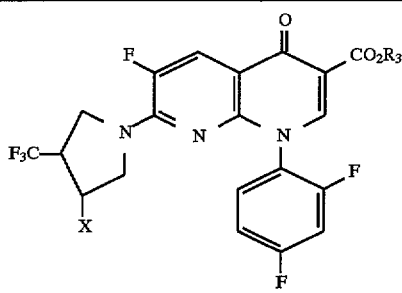

| Ex. No. | X | R₃ | Addition salt | Yield (%) | m.p. (°C.) | MS(M/Z) | $^1$H-NMR($\delta$) |
|---|---|---|---|---|---|---|---|
| 33a | NHBoc | Me |  | 96.5 | 130–133 | 586(M⁺), 512, 454, 411 | 1.45(9H, s), 3.05(1H, br m), 3.49–3.63(2H, br m), 3.84(2H, br m), 3.90(3H, s), 4.41(1H, br m), 5.21(1H, br m), 7.03–7.12(2H, m), 7.35–7.43(1H, m), 7.99(1H, d, J=12.5Hz), 8.42(1H, s) |
| 35a | NH₂ | H | .CF₃COOH | 93.2 | 221–223 | 472(M⁺), 428, 342, 290 | 3.35–3.98(6H, m), 7.32–7.38(1Hm, m), 7.55–7.62(1H, m), 7.78–7.86(1H, m), 8.17(1H, d, J=12.5Hz), 8.85(1H, s) |

Test Example

[Antibacterial Activity]

Antibacterial activities of the compounds of the present invention were measured as the minimum inhibitory concentration (MIC) by the agar plate dilution assay method according to the standard method of Japan Society of Chemotherapy. Ofloxacin (OFLX) was used as the control compound. The results are shown in Table 4.

TABLE 4

| | Minimum Inhibitory Concentration (MIC) | | | | | |
|---|---|---|---|---|---|---|
| Ex. | Tested Bacteria | | | | | |
| No. | a | b | c | d | e | f |
| 6a | 0.025 | 0.39 | 0.39 | 0.39 | 0.05 | 3.13 |
| 7a | ≦0.006 | 0.1 | 0.2 | 0.39 | 0.013 | 0.39 |
| 8a | ≦0.006 | 0.39 | 0.2 | 0.2 | 0.013 | 3.13 |
| 9a | ≦0.006 | 0.2 | 0.2 | 0.39 | 0.013 | 0.78 |
| 12a | 0.013 | 0.025 | 0.1 | 0.05 | 0.025 | 0.78 |
| 15a | ≦0.006 | 0.013 | 0.1 | 0.05 | 0.013 | 0.39 |
| 18a | ≦0.006 | 0.013 | 0.05 | 0.025 | ≦0.006 | 1.56 |
| 21a | 0.013 | 0.025 | 0.1 | 0.1 | 0.013 | 0.78 |
| 23a | 0.1 | 0.78 | 0.78 | 0.2 | 0.2 | 12.5 |
| 26a | 0.05 | 0.39 | 0.39 | 0.2 | 0.05 | 3.13 |
| 29a | 0.025 | 0.2 | 0.39 | 0.05 | 0.05 | 25 |
| 31a | 0.05 | 0.39 | 0.39 | 0.39 | 0.05 | 3.13 |
| 35a | 0.05 | 0.39 | 0.78 | 0.78 | 0.1 | 25 |
| 6b | ≦0.006 | 0.2 | 0.2 | 0.2 | 0.013 | 1.56 |
| 7b | ≦0.006 | 0.1 | 0.1 | 0.39 | 0.013 | 0.39 |
| 9b | ≦0.006 | 0.05 | 0.1 | 0.39 | ≦0.006 | 0.39 |
| 12b | ≦0.006 | ≦0.006 | 0.025 | 0.025 | ≦0.006 | 0.39 |
| 15b | ≦0.006 | 0.013 | 0.025 | 0.025 | ≦0.006 | 0.2 |
| 21b | ≦0.006 | ≦0.006 | 0.05 | 0.05 | ≦0.006 | 0.2 |
| 24b | 0.1 | 0.78 | 0.78 | 0.1 | 0.2 | 6.25 |
| 27b | 0.05 | 0.39 | 0.39 | 0.2 | 0.05 | 3.13 |
| 32b | 0.025 | 0.39 | 0.39 | 0.2 | 0.05 | 1.56 |
| OFLX | 0.2 | 0.78 | 1.56 | 0.1 | 0.39 | 25 | a: S. aureus Smith
b: S. pyogenes Cook
c: E. faecalis 1373
d: E. coli JC-3
e: S. aureus JS-1 (MRSA)
f: S. aureus KP-90-3 (MRSA)

[Acute Toxicity]

Acute toxicity test was performed using 6-week-old ICR mice. The compound of Example 21a was used as the tested compound. The compound was suspended in a 0.5% solution of methylcellulose, and the suspension was orally administered. The value of LD₅₀ was at least 4000 mg/kg.

[Mutagenicity]

Micronucleus assay was performed using 8-week-old ICR mice to confirm whether the compounds have mutagenicity. The compound of Example 21a was suspended in olive oil, and the suspension was abdominally administered to mice. The peripheral blood was obtained before and 24, 48 and 72 hours after the administration, and smeared specimens of the peripheral blood were prepared by acridine orange dying. In each specimen, 1000 erythrocytes were observed and frequency of occurrence of micronucleus was recorded. The frequency was not changed even in dose 200 mg/kg.

INDUSTRIAL APPLICABILITY

The quinolinecarboxylic acid derivatives of the present invention have strong antibacterial activities against MRSA as well as strong antibacterial activities against gram-positive bacteria such as Streptococcus and Enterococcus, so they can be used as a medicine, an antibacterial drug for animals or fishes, a preservative for foods and an agricultural chemical.

We claim:

1. A quinolinecarboxylic acid derivative or a salt thereof represented by the formula

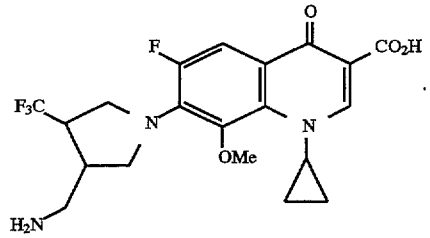

2. The quinolinecarboxylic acid derivative or a salt thereof according to claim 1 wherein the derivative is 7-(trans-3-aminomethyl-4-trifluoromethyl-1-pyrrolidinyl)-1-cyclopropyl-6-fluoro-1,4-dihydro-8-methoxy-4-oxoquinoline-3-carboxylic acid.

3. The quinolinecarboxylic acid derivative or a salt thereof according to claim 1 wherein the derivative is 7-(cis-3-aminomethyl-4-trifluoromethyl-1-pyrrolidinyl)-1-cyclopropyl-6-fluoro-1,4-dihydro-8-methoxy-4-oxoquinoline-3-carboxylic acid.

4. An antibacterial agent which comprises the quinolinecarboxylic acid derivative or a salt thereof according to claim 1 as an active ingredient.

5. An antibacterial agent which comprises the quinolinecarboxylic acid derivative or a salt thereof according to claim 2 as an active ingredient.

6. An antibacterial agent which comprises the quinolinecarboxylic acid derivative or a salt thereof according to claim 3 as an active ingredient.

7. A method for treating a bacterial infectious disease wherein the quinolinecarboxylic acid derivative or a salt thereof according to claim 1 is used.

8. A method for treating a bacterial infectious disease wherein the quinolinecarboxylic acid derivative or a salt thereof according to claim 2 is used.

9. A method for treating a bacterial infectious disease wherein the quinolinecarboxylic acid derivative or a salt thereof according to claim 3 is used.

* * * * *

UNITED STATES PATENT AND TRADEMARK OFFICE
CERTIFICATE OF CORRECTION

PATENT NO. : 5,668,147
DATED : September 16, 1997
INVENTOR(S) : NAKANO, et al

It is certified that error appears in the above-identified patent and that said Letters Patent is hereby corrected as shown below:

Column 4, line 36, "acetonitril" should read -- acetonitrile --.
Column 7, line 39, "palladium carbon" should read -- palladium on carbon --.
Column 8, line 30, "palladium carbon" should read --palladium on carbon--.
Column 8, line 33, "34" should read --34--.
Column 9, line 57, "palladium carbon" should read --palladium on carbon--.
Column 11, line 62, "palladium carbon" should read --palladium on carbon--.
Column 13, line 50, "butoxycarbony" should read --butoxycarbonyl--.
Column 14, lines 16-17, "palladium carbon" should read --palladium on carbon--.
Column 14, line 44, "conc-hydrochloride" should read --conc-hydrochloric acid--.
Column 15, line 1, "palladium carbon" should read --palladium on carbon--.
Column 15, line 1, "conc-hydrochloride" should read --conc-hydrochloric acid--.
Column 16, line 46, "palladium carbon" should read --palladium on carbon--.

UNITED STATES PATENT AND TRADEMARK OFFICE
CERTIFICATE OF CORRECTION

PATENT NO. : 5,668,147
DATED : September 16, 1997
INVENTOR(S) : NAKANO et al.

It is certified that error appears in the above-identified patent and that said Letters Patent is hereby corrected as shown below:

Columns 21-22, 23-24 and 25-26, TABLE 2:

" 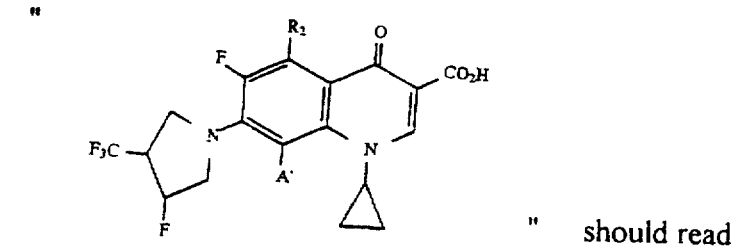  " should read

-- 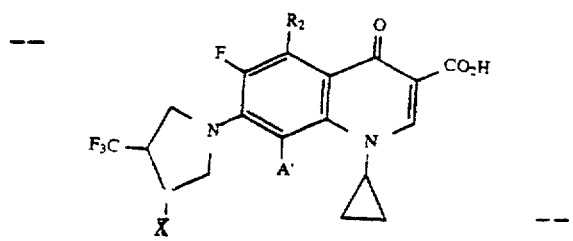 --

Signed and Sealed this

Sixth Day of July, 1999

Attest:

Q. TODD DICKINSON

*Attesting Officer*    Acting Commissioner of Patents and Trademarks